United States Patent [19]

Hulme

[11] 4,283,949
[45] Aug. 18, 1981

[54] DILUTE SOLUTION APPARATUS

[75] Inventor: Joseph M. Hulme, Sarnia, Canada

[73] Assignee: Polysar Limited, Sarnia, Canada

[21] Appl. No.: 100,394

[22] Filed: Dec. 5, 1979

[30] Foreign Application Priority Data

Mar. 28, 1979 [CA] Canada .................................. 324301

[51] Int. Cl.$^3$ .............................................. G01N 1/14
[52] U.S. Cl. ................... 73/864.34; 73/864; 73/864.12
[58] Field of Search ........ 73/61.1 C, 423 A, 422 GC; 137/99, 565; 222/136

[56] References Cited

U.S. PATENT DOCUMENTS

| | | | |
|---|---|---|---|
| 2,413,029 | 4/1977 | Carlyle | 137/99 |
| 3,012,863 | 12/1961 | Feichtmeir | 73/425.6 |
| 3,934,456 | 1/1976 | Munk | 73/61.1 C |
| 4,002,070 | 1/1977 | Howell | 137/565 |

Primary Examiner—S. Clement Swisher
Attorney, Agent, or Firm—Stevens, Davis, Miller & Mosher

[57] ABSTRACT

An apparatus is provided for the preparation of a dilute solution of a sample of a fluid comprising a valve means communicating with a dilution means, a line to the dilution means to supply diluent thereto from a reservoir, a line in communication with the valve means to remove diluted sample from the dilution means through the valve means, a line in communication with the dilution means having a valve for connection to a supply of compressed gas thereto or for connection to atmospheric pressure flow control means to control flow of diluent from the reservoir to the dilution means, and control means for controlling operation of the valve means, the valve and the flow control means. The apparatus is useful for obtaining dilute solutions of polymer cements for subsequent composition or property determination.

4 Claims, 5 Drawing Figures

DILUTE SOLUTION APPARATUS

This invention relates to apparatus for the sampling and dilution of a sample from a fluid stream, especially to apparatus for sampling and dilution of hydrocarbyl streams containing dissolved therein a polymeric material.

The manufacturing industry has a continuing requirement to obtain samples which are representative of a wide variety of fluid streams in order that the composition and/or properties of the stream may be determined. The composition or properties of the stream may include the polymer content of a solution of the polymer such as from the effluent of a polymerization reactor, it may be the composition and/or concentration of one or more components such as from the reaction in solution of one or more materials to produce product or products, it may be the composition and/or concentration of one or more components in a diluent such as from a hydrocarbon cracking operation, and it may be the concentration of one or more components in a diluent such as from a dissolving operation. The sample obtained must be representative of the stream from which it is obtained and the sample may be subjected to a wide variety of subsequent operations which require dilution of the original sample. Such dilution may be for an analytical purpose where only a small sample is necessary for example, as in a chromatographic or mass spectrometric analysis or for a solution viscosity measurement.

One objective of this invention is to provide an apparatus for the preparation of a dilute solution of a sample of a fluid. A further objective is to provide an apparatus for the removal of a sample of a fluid and the dilution of said sample. A still further objective of the invention is to provide an apparatus for the removal of a sample of a fluid from a line containing said fluid and diluting said sample by the addition of a fixed amount of a diluent therefor.

In accordance with the invention, there is provided an apparatus for the preparation of a dilute solution of a sample of a fluid which apparatus comprises a value means communicating with a dilution means, a line to said dilution means to supply diluent from a reservoir to said dilution means, a line in communication with said valve means to remove diluted sample from said dilution means through said valve means, a line in communication with said dilution means having a valve for connection to a supply of compressed gas or for connection to atmospheric pressure, flow control means to control flow of diluent from said reservoir to said dilution means, and control means for controlling operation of said valve means, said valve and said flow control means, wherein said valve means comprises a two-position valve having a housing equipped with ports, the chamber of said housing containing a movable two-position valve core equipped with flow channels each of which separately communicates with two adjacent ports, a first port being in communication with inlet means for said fluid, a second port being in communication with an outlet means for said fluid, a third port being in communication with said dilution means, a fourth port being in communication with the diluted sample in said dilution means and a fifth port being for removal of said diluted sample from the apparatus, a first said flow channel communicating in its first position with said first and second ports and in its second position with said second and third ports and a second flow channel communicating in its first position with said third and fourth ports and in its second position with said fourth and fifth ports, and wherein said dilution means comprises a narrow diameter cylindrical chamber connected at its upper end to the third port of said valve means and connected at its lower end to a wide diameter closed cylindrical chamber which has at the side wall at its lower end a line in communication with the fourth port of said valve means and said reservoir and has at its upper end a line having a valve therein whereby said line may be connected to a supply of compressed gas, or to the atmosphere, said narrow diameter cylindrical chamber having located concentrically therein and axially slidably movable within a close fitting plunger equipped with seals to prevent leakage and having at its lower end depending into said wide diameter chamber a flange end for abutting engagement with the under surface of the wide diameter chamber at the point where the narrow diameter cylindrical chamber is attached to the wide diameter chamber, and said wide diameter closed cylindrical chamber having concentrically located therein and axially slidably movable within a close fitting, double acting barrier piston equipped with seals to prevent fluid leakage and having a stirring means located within said wide diameter chamber and below said double acting barrier piston.

A better understanding of the invention will follow from a consideration of the drawings which describe embodiments of the invention.

Figure 1:
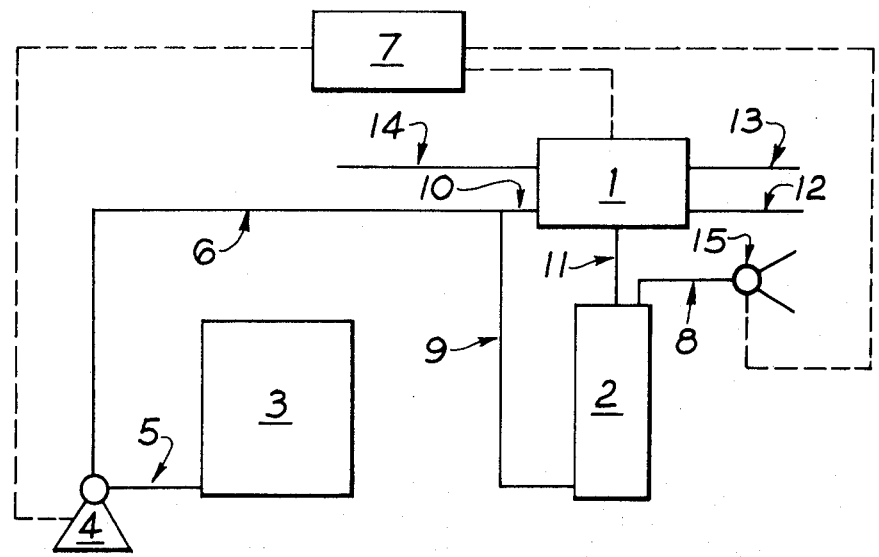
FIG. 1 is a schematic diagram of the apparatus.

Referring to FIG. 1, a valve means 1 controls the flow of fluid into the apparatus. Fluid flows into the valve means by line 12 and may be directed out of the valve means by line 13 or may be directed into the dilution means 2 by cylinder 11 which forms a part of the dilution means. Line 14 is for removal of the diluted sample from the dilution means via line 9 to line 10 into valve means 1 and into line 14. Reservoir 3 provides storage for the diluent, the flow of which is controlled by pump 4 through line 5 and pump 4 into line 6 and through line 9 into the dilution means. Line 8 connects the dilution means to valve 15 whereby line 8 may be connected to a supply of compressed gas or to the atmosphere. Control means 7 controls the operation of pump 4 and directs the operation of valve means 1 and the valve 15.

Figure 2:
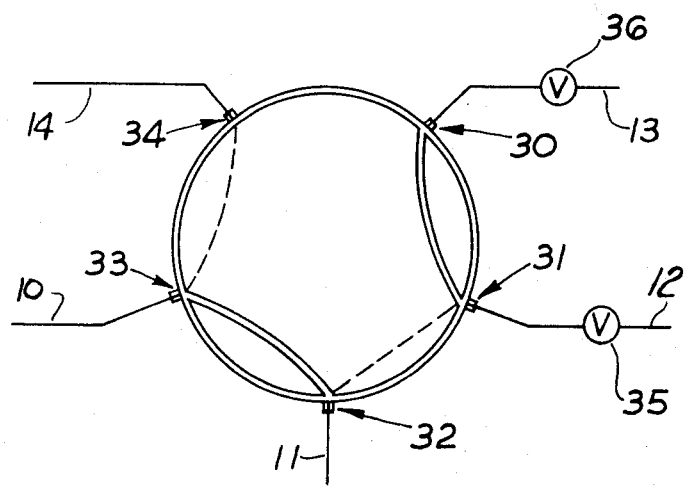
FIG. 2 is a schematic diagram of a valve means for obtaining fluid samples.

FIG. 2 is a schematic diagram of a valve means for use as valve means 1 of FIG. 1. The valve means is a two-position valve with a housing equipped with 5 ports, 30, 31, 32, 33 and 34 spaced at about 72° intervals around the housing, the chamber of said housing containing a movable two-position valve core rotatable through about 72°. The valve core contains two flow channels. In a first position of said valve core, a first such flow channel is shown connecting ports 30 and 31 and the second such flow channel is shown connecting ports 32 and 33. On rotation of the valve core through about 72° to its second position, the first flow channel connects port 31 to port 32 and the second flow channel connects port 33 to port 34, as is shown by the dotted lines. Line 12 connected to port 31 supplies the fluid to the valve means and line 13 connected to port 30 is for removal of excess fluid sample, the flow of fluid being through the first flow channel in the valve core as shown in the figure. Valves 36 and 37 control the flow of fluid in lines 12 and 13 respectively. Cylinder 11 is connected to port 32; cylinder 11 is part of the dilution means and connects the valve means to the dilution means. Line 10 is for transfer of the sample and for transfer of the diluted sample from the dilution means into port 33 and through the second flow channel in the second position of the valve core (as shown by the dotted line) to port 34 and out of the valve means by line 14. It will be readily apparent to one of average skill in the art that a variety of valve means may be utilized, including two-position valves with rotatable cores and two-position valves with axially movable cores.

Figure 2A:
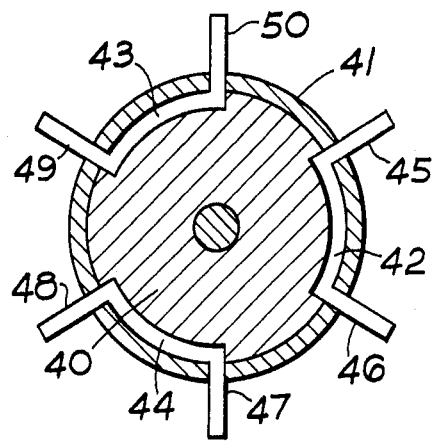
FIG. 2a is a diagram of a suitable valve means for obtaining fluid samples.

FIG. 2a is a suitable valve means for use as valve means 1 of FIG. 1. The valve means is a two-position valve which comprises a housing 41 equipped with six ports spaced at intervals of about 60° and a valve core 40 rotatable through about 60°. To the housing there are attached at each of the six ports lines 45, 46, 47, 48, 49 and 50. The valve core contains three flow channels 42, 43 and 44. The Figure shows line 45 (which may correspond to line 13 of FIG. 2) connected by flow channel 42 to line 46 (which may correspond to line 12 of FIG. 2). Similarly, line 47 (which may correspond to cylinder 11 of FIG. 2) is shown connected by flow channel 44 to line 48 (which may correspond to line 10 of FIG. 2) and line 49 (which may correspond to line 14 of FIG. 2) is shown connected by flow channel 43 to line 50, which is a spare line not necessary to the operation of the apparatus. By rotation of the valve core through about 60° to its second position, line 46 may be connected by flow channel 42 to line 47 and line 48 may be connected by flow channel 44 to line 49.

Figure 2B:
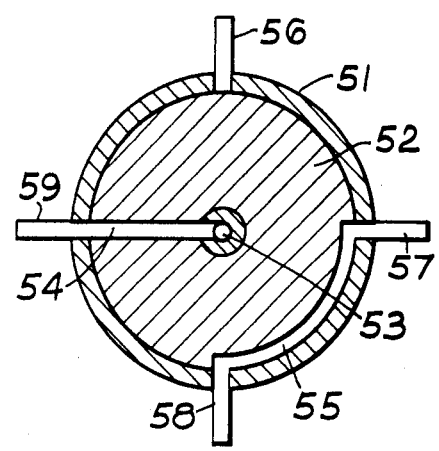
FIG. 2b is a diagram of a preferred valve means for obtaining fluid samples from a continuous flow of the sample fluid.

FIG. 2b is a preferred valve means for use in the apparatus when the fluid is available as a continuous flowing stream. The valve means is a two-position valve which comprises a housing 51 equipped with four ports spaced at intervals of about 90° and a pneumatically operated two-position valve core 52 which is movable by rotation through about 90°. The housing 51 has attached at each of the ports lines 56, 57, 58 and 59. Perpendicular to the plane of the paper is line 53 which is attached to the valve core. The valve core contains two flow channels 54 and 55. Flow channel 54 is directly connected to line 53 (corresponding to line 12 of FIG. 2) which is the source of supply of the fluid. As shown in the Figure, flow channel 54 is connected to line 59 (which corresponds to line 13 of FIG. 2) which returns the supply of fluid to the continuous flowing stream. The figure shows line 57 connected by flow channel 55 to line 58. To obtain a sample of the fluid, the valve core is rotated through about 90° to its second position to connect line 53 via flow channel 54 to line 58 (which corresponds to cylinder 11 of FIG. 2) which is part of the dilution means. On rotation of the valve core back to its first position as shown in the figure, the fluid sample retained in line 58 is removed from line 58 through flow channel 55 and line 57 (which corresponds to line 10 of FIG. 2) to the dilution means and is mixed with diluent. The diluted sample is removed from the dilution means by rotation of the valve core through about 90° to its second position to connect line 53 by flow channel 54 to line 58 whereby a new sample of the fluid is obtained and the diluted sample from the dilution device passes through line 57 via flow channel 55 (which now connects lines 57 and 56) to line 56 (which corresponds to line 14 of FIG. 2) and out of the valve means.

Figure 3:
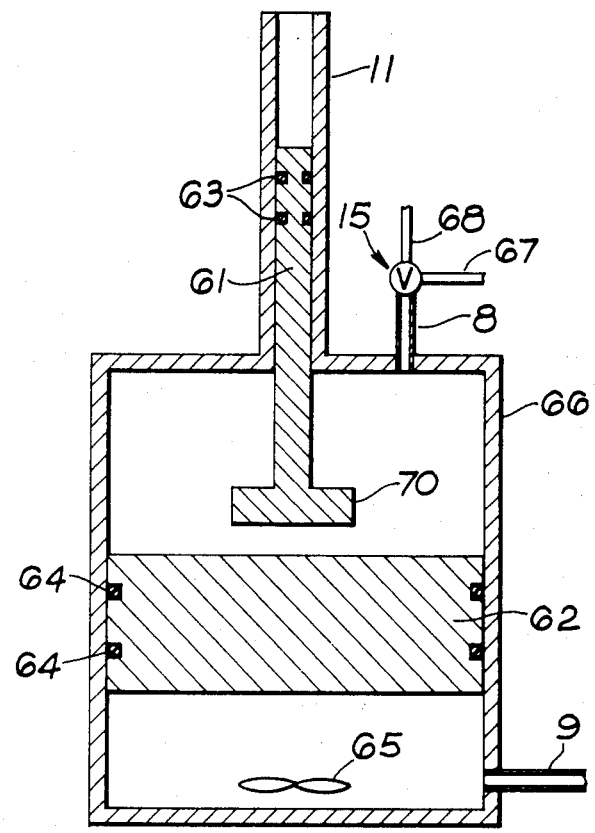
FIG. 3 is a diagram of a dilution means.

FIG. 3 is a dilution means suitable for use in the apparatus. A narrow diameter cylinder 11, forming a narrow diameter cylindrical chamber, is attached at its upper end to the valve means (line 11 of FIGS. 1 and 2) and at its lower end to a wide diameter closed cylinder 66 with end walls and defining a wide diameter closed cylindrical chamber. The narrow diameter cylinder has located concentrically therein and axially slidably movable within the cylindrical chamber a close-fitting plunger 61 equipped with seals 63 to prevent fluid leakage and having at its lower end depending into the wide diameter cylindrical chamber a flange end 70 for an abutting engagement with the under surface of the wide diameter chamber at the point where the cylinder is attached to the wide diameter chamber. The wide diameter closed cylindrical chamber has concentrically located therein and axially slidably movable within said chamber a close-fitting, double-acting barrier piston 62, equipped with seals 64 to prevent fluid leakage, for separating the chamber into two parts and for providing drive to push the plunger 61 upwardly into the cylinder 11 or to push fluid downwardly out of the chamber. The chamber is equipped with a line 8 at the upper end wall of the chamber, line 8 being connected to valve 15 whereby line 8 may be connected to a supply of compressed gas 67 to push the barrier piston downwardly in the chamber or to the atmosphere by line 68 in order to vent compressed gas and permit upward movement of the barrier piston. The upward movement of the barrier piston is limited by contact with flange 70 of plunger 61 in its uppermost position of abutting engagement with the under surface of the wide diameter chamber and the downward movement of the barrier piston is limited by contact with the stirring bar 65. At the lower end of the chamber and attached to a lower portion of the wall thereof is line 9 for supply of diluent and sample to the chamber and for removal of the diluted sample from the chamber. Within the chamber and below the barrier piston is a stirring means which is a magnetic stirring bar 65 which is activated by an external controlled speed stirring device of known form (not shown).

In an operation of the apparatus and with reference to FIGS. 1, 2 and 3, the control means 7 causes the valve core to be set in its first position, the pump to be set in the off condition and the barrier piston of the dilution means to be at its lowest point of travel with valve 15 open to the atmosphere. The fluid to be sampled is passed (FIGS. 1 and 2) through line 12 into valve means 1 and out through line 13 to flush out the lines with the valve core in its first position. Control means 7 causes the valve core (FIG. 2) to be rotated to its second position so that line 12 is connected by the flow channel to cylinder 11 of the dilution means. A sample of the fluid flows into cylinder 11, forcing the plunger 61 therein downward until the flange end is in contact with the barrier piston 62 which is located at the lowest point of its travel within chamber 66. Control means 7 causes the valve core to be rotated back to its first position, as shown in FIG. 2, and pump 4 (FIG. 1) to be activated causing the diluent to flow from the reservoir 3 through line 6 and line 9 into the bottom of the chamber (FIG. 3) of the dilution means. The flow of diluent into the chamber forces the barrier piston 62 to move upwardly within the chamber and the upward movement of the barrier piston forces the plunger 61 to move upwardly within the cylinder 11 thus displacing the fluid sample from cylinder 11 through the flow channel into line 10 where at the junction of lines 6 and 10 (FIG. 1) it is mixed with and flows with the diluent through line 9 into the bottom of the chamber of the dilution means (FIG. 3). With the stirring means in the bottom of the chamber of the dilution means activated, the diluent and sample become well mixed. When the barrier piston has been displaced to its uppermost point within the chamber, control means 7 deactivates the pump thereby stopping the flow of the diluent into the dilution means and causes the valve core to be rotated to its second position. Control means 7 activates valve 15 so that compressed gas is supplied to line 67 of the dilution means thus forcing the barrier piston in a downward motion causing the displacement of the diluted sample from the chamber through line 9 and, see FIG. 1, into line 10 through the valve means to line 14 and thence to whatever analytical or property measuring means desired. By these operations, a constant volume of the fluid is obtained, a constant fraction of this volume is diluted with a constant volume of diluent and is available for subsequent use. By suitable choice of the volume of cylinder 11 and chamber 66, it is possible to achieve the extent of dilution required.

Suitable fluids which may be sampled and diluted include, but are not limited to, solutions of synthetic polymers. Suitable polymers may include polybutadiene, polyisoprene and ethylene-propylene-diene monomer polymers. Suitable diluents may include any one of or mixtures of benzene, toluene, hexane, butene, cyclohexane and tetrahydrofuran.

In illustration of the operation of the apparatus of the invention, samples were taken and dilute samples prepared of polybutadiene cement. The polybutadiene cement was obtained from a polymerization chain, at various polymer concentrations, the cement containing polybutadiene, ureacted butadiene, benzene and butene-1. The diluent used was cyclohexane.

The valve means was a pneumatically operated two-position valve having six ports, as illustrated in FIG. 2a. The volume of each of the flow channels was about 10 microliters. The dilution means, constructed from brass for certain experiments and from stainless steel for other experiments, was attached by its narrow diameter cylinder (FIG. 3) directly to the port of the valve means. The narrow diameter cylindrical chamber had an internal diameter of 3.5 mm and was 54.5 mm long. The plunger concentrically located within the narrow diameter cylinder had an outside diameter just under 3.5 mm and was equipped with two VITON ® O-rings. The plunger had an enlarged flange end of 12.5 mm length and 9.5 mm diameter. The wide diameter cylindrical chamber had an internal diameter of 22.5 mm and was 73.5 mm long. The barrier piston concentrically located within the chamber was 16.5 mm long, had a diameter of just under 22.5 mm and was equipped with two VITON ® O-rings. The stirrer inside the bottom of the chamber was a 20 mm length of thin soft iron wire encapsulated in TEFLON ®. When the plunger was fully displaced downward, the volume of fluid sample contained in the narrow cylinder was 0.3 ml. When the barrier piston was fully displaced upward the volume of dilute solution contained therein was 15.35 ml. The control means for controlling the operation of the apparatus was a micro computer.

For calibration purposes, samples of polybutadiene were made up into solutions of various concentrations and used as the fluid to be sampled in the apparatus. The concentration of polymer in the diluted sample was measured and compared to that expected knowing the dilution ratio and the original polymer content of the solutions. Using original solutions containing from about 5 to about 20 weight percent of polybutadiene, the error associated with the concentration of polymer in the diluted sample was determined to be less than about one percent, showing that the apparatus is capable of providing a diluted sample with great accuracy and repeatability.

Polybutadiene cement from a polymerization reactor, as described above, was sampled into the apparatus and the diluted sample was supplied to a gel permeation chromatographic unit for determination of molecular weight distribution. Samples of the diluted sample were also taken for determination of the polymer content in order to check the accuracy and repeatability of use of the apparatus. The results showed the error to be less than about 1.5 percent.

Butyl polymer dissolved in hexane may be similarly sampled and diluted and the concentration of polymer in the diluted sample determined.

What is claimed is:

1. An apparatus for the preparation of a dilute solution of a sample of a fluid which apparatus comprises a valve means communicating with a dilution means, a line to said dilution means to supply diluent from a reservoir to said dilution means, a line in communication with said valve means to remove diluted sample from said dilution means through said valve means, a line in communication with said dilution means having a valve for connection to a supply of compressed gas thereto or for connection to atmospheric pressure, flow control means to control flow of diluent from said reservoir to said dilution means, and control means for controlling operation of said valve means, said valve and said flow control means, wherein said valve means comprises a two-position valve having a housing equipped with ports, the chamber of said housing containing a movable two-position valve core equipped with flow channels each of which separately communicates with two adjacent ports, a first port being in communication with inlet means for said fluid, a second port being in communication with an outlet means for said fluid, a third port being in communication with said dilution means, a fourth port being in communication with the diluted sample in said dilution means and a fifth port being for removal of said diluted sample from the apparatus, a first said flow channel communicating in its first position with said first and second ports and in its second position with said second and third ports and a second flow channel communicating in its first position with said third and fourth ports and its second position with said fourth and fifth ports, and wherein said dilution means comprises a narrow diameter cylindrical chamber connected at its upper end to the third port of said valve means and connected at its lower end to a wide diameter closed cylindrical chamber which has at the side wall at its lower end a line in communication with the fourth port of said valve means and said reservoir and has at its upper end a line having a valve therein whereby said line may be connected to a supply of compressed gas or to the atmosphere, said narrow diameter cylindrical chamber having located concentrically therein and axially slidably movable within a close fitting plunger equipped with seals to prevent fluid leakage and having at its lower end depending into said wide diameter chamber a flange end for abutting engagement with the under surface of the wide diameter chamber at the point where the narrow diameter cylindrical chamber is attached to the wide diameter chamber, and said wide diameter closed cylindrical chamber having concentrically located therein and axially slidably movable within a close fitting, double acting barrier piston equipped with seals to prevent fluid leakage and having a stirring means located within said wide diameter chamber and below said double acting barrier piston.

2. The apparatus of claim 1 wherein the valve means is a pneumatically operated two-position valve comprising a housing equipped with six ports spaced at intervals of about 60° and a valve core rotatable through about 60° and having three flow channels.

3. The apparatus of claim 1 wherein the valve means is a pneumatically operated two-position valve comprising a housing equipped with four ports spaced at intervals of about 90° and a valve core rotatable through about 90° having a line attached perpendicular to said valve core and directly connected to one flow channel and equipped with a second flow channel.

4. The apparatus of claim 1 wherein the control means is a micro computer.

* * * * *